United States Patent [19]

Prudden

[11] 4,006,224

[45] Feb. 1, 1977

[54] METHOD AND AGENT FOR TREATING INFLAMMATORY DISORDERS OF THE GASTROINTESTINAL TRACT

[75] Inventor: John Fletcher Prudden, Upper Nyack, N.Y.

[73] Assignee: Lescarden Ltd., Goshen, N.Y.

[22] Filed: Sept. 29, 1975

[21] Appl. No.: 617,741

[52] U.S. Cl. .............................. 424/180; 424/325
[51] Int. Cl.² ................ A61K 31/13; A61K 31/70
[58] Field of Search .......................... 424/325, 180

[56] References Cited

UNITED STATES PATENTS

| | | | |
|---|---|---|---|
| 3,232,836 | 2/1966 | Carlozzi et al. | 424/180 |
| 3,683,076 | 8/1972 | Rovoti | 424/180 |
| 3,912,714 | 10/1975 | Kulbakh | 424/180 |

*Primary Examiner*—Stanley J. Friedman
*Attorney, Agent, or Firm*—Darby & Darby

[57] ABSTRACT

A method for alleviating inflammatory diseases of the gastro intestinal tract by administration of a composition containing a D-glucosamine salt of a pharmaceutically acceptable acid. The invention also pertains to a new mode of administering D-glucosamine for treatment of inflammatory disorders of the gastrointestinal tract.

18 Claims, No Drawings

METHOD AND AGENT FOR TREATING INFLAMMATORY DISORDERS OF THE GASTROINTESTINAL TRACT

This invention relates to methods of treating non-specific granulomatous inflammatory diseases afflicting the wall of the gastrointestinal tract in mammals. More specifically, the invention pertains to the treatment of regional enteritis and ulcerative colitis in mammals.

Regional enteritis is a non-specific granulomatous disease sometimes referred to as Crohn's disease which usually affects the lower ileum but may involve other portions of the gastrointestinal tract. Ulcerative colitis is an inflammatory disorder of the colon characterized by the passage of bloody or purulent mucus alone or accompanying diarrhea or formed stools. Both diseases are characterized by inflammation of the affected portion of the gastrointestinal tract, hyperemia and edema. In many instances abscesses, internal, and external fistulas are also apparent. The etiology of both disorders is unknown but most frequently they attack young adults aged 20 to 40. Severe abdominal cramps, diarrhea, anorexia, and fluctuating fevers are frequently found in both conditions.

Since no specific cure is known for either disorder, treatment is currently limited to corticosteroid thereapy to reduce the inflammation of surgery to resect the involved organ segments or to by-pass the diseased area. Although corticosteroid therapy induces remission in many cases, prolonged administration of such drugs (e.g. ACTH, Prednisone) can result in serious side effects including muscle wasting, internal bleeding and impairment of the body's normal wound healing abilities. Accordingly, long-term corticosteroid thereapy is not recommended.

Surgery is often necessary when intestinal obstruction, abscesses or fistulas are present, or when severe hemorrhaging has commenced. However, surgery does not cure regional enteritis and the post-operative recurrence rate is greater than 50% within five years. Post-operative recurrence of the disease is usually more severe than prior to the surgical procedure. In the case of ulcerative colitis, removal of the afflicted bowel segments may result in the imposition of an additional strain upon the remaining portions of the organ in which the disease may then occur. As in the case of regional enteritis, surgery does not cure the disease but only controls complications.

Salicylazosulfapyridine has also been used to treat mild forms of ulcerative colitis with some success, however prolonged administration of this medicament can lead to anorexia, and it is not effective until several weeks after administration.

Although current theory indicates that both disorders are autoimmune type diseases related to asthma and similar conditions, administration of conventional antihistamine medicaments does not relieve the symptoms or lead to remission in either disease.

It has now been surprisingly discovered that D-glucosamine, may be administered orally and parenterally to treat inflammatory disorders of the gastrointestinal wall and to provide results which are at least equal to and in most instances superior than those obtained with prior art treatments.

Accordingly, an important object of the present invention is the provision of an improved method of treating inflammatory diseases of the gastrointestinal tract. In the context of this invention the term "gastrointestinal tract" refers to the stomach, small bowel and colon.

Another aspect of the present invention relates to a novel method of administering D-glucosamine solutions in the treatment of ulcerative colitis and regional enteritis.

A still further aspect of the present invention is to provide a method of treating inflammatory disorders of the gastrointestinal tract by the administration of an effective amount of a composition containing a pharmaceutically acceptable acid salt of D-glucosamine.

Yet another aspect of the present invention involves the provision of a method for treating ulcerative colitis and regional enteritis by the subcutaneous administration of D-glucosamine hydrochloride depots in distensible areas of the body.

These and other objects of the present invention will become apparent upon consideration of the following detailed description of the invention.

The process of the present invention involves administering an effective amount of a composition containing a pharmaceutically acceptable acid salt of D-glucosamine to a subject afflicted with an inflammatory disorder of the gastro-intestinal tract.

D-glucosamine is a 2-amino derivative of glucose and is obtained on chemical hydrolysis of chitin, a polysaccharide which forms the hard shell of crustaceans and insects. As taught in U.S. Pat. No. 3,232,836 Glucosamine is useful to facilitate the healing of surgical wounds of the body surface. D-glucosamine (2-amino-D-glucose) is an amino sugar which readily dissolves in water or isotonic (about 0.1%) saline solution. In the present invention the active agent D-glucosamine is employed in the form of a salt of glucosamine with pharmaceutically acceptable acids, preferably D-glucosamine hydrochloride. Such compositions are formed by reacting D-glucosamine with a pharmaceutically acceptable acid, e.g., hydrochloric, citric, malic, phosphoric, etc., in well known fashion to neutralize the amine.

The active agent of the invention may be administered in the form of a liquid as a suspension or solution, or alternatively in solid form as a tablet, pellet, or capsule. Suspensions or solutions of the active ingredient in pharmaceutically acceptable liquids are suitable for oral administration. Satisfactory pharmaceutically acceptable liquids include water, sugar solutions, and aqueous glycols which may be compounded with coloring agents and synthetic or natural flavors. Alternatively, the active ingredient may be administered in a solid form such as a pellet, capsule or tablet. The tablets may be prepared in accordance with conventional tabletting procedures in which the active ingredient is combined with well known pharmaceutical excipients such as starch, sugar, bentonite clays, and other commonly used carriers. In another embodiment, the active ingredient may be incorporated onto silica gel or other gel forming materials which are capable of coating the stomach walls. A preferred mode of oral administration is in a solid form (as a tablet) although aqueous suspensions or syrup formulations are also employed with great success.

The active ingredient may also be administered parenterally, that is, subcutaneously, as a sterile solution. Preferably D-glucosamine hydrochloride is administered in aqueous solutions at a concentration between about 1% and about 30% of the active ingredient and preferably between about 10% and 20%. Injectable dosage forms for intravenous administration are generally prepared by dissolving the desired quantity of D-glucosamine in an isotonic (approximately 0.9%) saline solution. In the preferred subcutaneous depot administration technique described below, the aqueous injectable dosage form is prepared by simply dissolving the pharmaceutically acceptable acid salt of D-glucosamine (preferably D-glucosamine hydrochloride) in sterile water.

The effective dosage (for either the oral or parenteral route of administration) for use in this invention depends upon the severity of condition, the stage and individual inflammatory characteristics of each human being treated. The compositions are generally administered in a dosage range of from about 20 milligrams to about 300 milligrams of active ingredient per kilogram of body weight per day and preferably from about 50 to about 150 milligrams per kilogram of body weight per day. The quantity of effective dose supplied by each capsule, tablet or injection is relatively unimportant since the total dosage can be reached by administration of either one or a plurality of capsules or tablets, or both, or by one or more injections.

The pharmaceutically acceptable acid salts which may be employed in the present invention include D-glucosamine salts of mineral acids such as hydrochloric, phosphoric and organic acids including for example citric, ascorbic, gluconic, malic, acetic and the like. D-glucosamine hydrochloride, the D-glucosamine salt of hydrochloric acid, is especially effective and hence preferred for use in both the oral and parenteral routes of administration.

Although the active ingredient of the invention may be administered via intravenous injection (in an isotonic saline solution), in the preferred route of parenteral administration a fairly large volume of aqueous D-glucosamine hydrochloride solution is subcutaneously injected into areas of the body possessing a readily distensible subcutaneous space, e.g., the back, anterior thorax, abdomen and anterior thighs, to form accretions or depots which are pronounced and palpable. Each depot should contain not less than about 10cc nor more than about 75cc of an aqueous solution of the active ingredient. In most instances, a subcutaneous depot containing about 30cc of 10% D-glucosamine hydrochloride solution has been found to give excellent results. Depot administration is carried out by subcutaneously injecting from about 10 to about 75cc and preferably about 30cc of a sterile aqueous D-glucosamine hydrochloride solution into a single subcutaneous site in a distensible body area. Preferably, more than one depot (usually two or three) is formed during each treatment. In a preferred embodiment a total of about 120cc of 10% Glucosamine Hydrochloride is subcutaneously injected by forming two 60cc depots at spaced apart points on the subject's body. Depot treatments are administered approximately once a week or as required to obtain remission from symptoms. Smaller amounts can be administered in a greater number of depot sites and/or at more frequent intervals in the interest of patient comfort. Administration is carried out at slow injection speed for the same reason. Within several hours after administration of a subcutaneous depot, the palpable subcutaneous mass comprising the medicament begins to disperse and becomes noticeably softer and less pronounced. This indicates that the material in the depot has begun to be absorbed by body tissues, probably through the lymphatic system, and will eventually be absorbed into the blood vascular system. To minimize the discomfort of a subject due to formation of a subcutaneous depot, the glucosamine solution is diluted approximately 1 to 10 with 1% lidocaine or an equivalent local anesthetic just prior to administration. In most instances, between about 4 and about 12 hours is required for the aqueous solution located in each depot to be absorbed in the tissues of the body and eventually into the bloodstream thereby dissipating the stored glucosamine deposit.

The following examples are illustrative of the manner for preparing solid and liquid glucosamine dosage forms having applications in the treatment of inflammatory gastrointestinal disroders.

EXAMPLE 1

A 10% D-glucosamine hydrochloride solution was prepared by dissolving 1 gram of sodium chloride and 100 grams of D-glucosamine hydrochloride in 1 liter of water. This solution is especially suitable for parental (intravenous) administration, but may also be used for depot injections.

EXAMPLE 2

A 20% Glucosamine Hydrochloride solution was prepared by dissolving 200 grams of D-glucosamine hydrochloride in sterile water. This solution is especially suitable for oral and parenteral (subcutaneous) depot administration, but may be used for slow intravenous injections as well.

EXAMPLE 3

100 grams of D-glucosamine hydrochloride (in powder form) was mixed with 250 grams of anhydrous lactose (direct tablet grade) and 16 grams of powdered corn starch (U.S.P. quality - passed through a No. 25 mesh steel screen) in a small pebble mill for 30 minutes and compressed on a single punch machine producing 1,000 tablets, each containing 50 milligrams active ingredient. Each tablet weighs approximately 375 milligrams.

As indicated previously, the glucosamine containing medicaments of the present invention successfully treat inflammatory disorders of the gastrointestinal tract, including for example, ulcerative colitis and regional enteritis as evidenced by symptomatic remission, weight gain, decreased stool frequency, relief from abdominal cramping, shrinkage of intestinal polyps (as confirmed by sigmoidoscopy and biopsy) and decreased inflammation. The length of symptomatic remission varies from patient to patient depending upon severity of the disease and the patient's particular condition. In some extremely severe cases, symptoms return within several days after treatment had ceased. However, in many instances patients have remained asymptomatic and were considered clinically free of disease for periods of several months and longer. Experience has shown that a patient requires from about 1 to about 20 grams per treatment of glucosamine (administered either orally or parenterally) for two or three successive treatments at the commencement of glucosamine therapy, followed by subsequent administration of greater or lesser quantities at varying intervals (tailored to the particular patient's response to treatment and condition) to achieve complete symptomatic remission. It is contemplated that the recurring autoimmune nature of most inflammatory gastrointestinal diseases and especially ulcerative colitis and regional enteritis may require administration of booster or maintenance dosages at periodic intervals.

A group of 9 patients suffering from regional enteritis or ulcerative colitis (i.e., individuals with confirmed inflammatory conditions and severe symptomology) were treated in a clinical situation by parenteral and/or oral administration of D-glucosamine hydrochloride according to the present invention. In most cases the patient received between about 50 and about 300 milligrams per kilogram of D-glucosamine hydrochloride (either in the form of an orally administered solution or via parenteral depot injection). The exact dosage and frequency of treatment was determined in each instance by the severity of the individual's condition and his response to the medication. Treatment was discontinued when the patient experienced a marked relief from symptoms and reinstituted upon their reappearance. Table A is a summary of case reports which demonstrate the results obtained with the therapeutic compositions of this invention.

TABLE A

| Patient Identification Sex & Age | DIAGNOSIS | THERAPY | RESULTS |
| --- | --- | --- | --- |
| 1. CT Female Age 48 | Crohn's Disease confirmed by Barium Enema - ACTH & Prednisone ineffective | 60cc Glucosamine HCL (10% SOLN) by subcutaneous injection into 2 depots - 3 treatments 1 week apart | All Intra-Abdominal Symptoms Stopped |
| 2. RF Female Age 53 | Severe Crohn's Disease - Recurrence following ileum resection (18 yrs ago) & ileo colectomy (8 yrs ago) despite ACTH & Prednisone | 20cc 10% Glucosamine - HCL subcutaneously in each of 2 depots once a week for one month then 40 cc 10% in each depot every 2 weeks for 2 mos. | complete symptomatic remission - gain in muscle mass, red cell mass, appetite and vigor |
| 3. TF Female Age 19 | Regional Enteritis - confirmed by X-Ray - recurrence following previous ileo-colectomy; steroid therapy not effective | 60cc 10% Glucosamine HCL subcutaneously in each of 2 depots once a week for 3 weeks then 60cc 10% orally per day | 10 lb weight gain - complete symptomatic remission |
| 4. RM Male Age 62 | Suffering from Crohn's Disease for 25 years - entire small bowel involved | 60cc 10% Glucosamine HCL in each of two subcutaneous depots once a week for 2 months then 60cc of 20% glucosamine twice a day | GI Series shows improvement - 10 lbs weight gain |
| 5. ES Female Age 47 | Ulcerative colitis Azulfidine, prednisone ACTH given with little effect | 20cc 10% Glucosamine HCL in each of two depots once a week for 6 mos. then 40cc in each depot every three weeks for 6 months then 30 cc 20% glucosamine HCL per day orally | Lower stool frequency - firm consistency |
| 6. DM Male Age 40 | Ulcerative Colitis - many polyps | 60cc 10% Glucosamine in each of 2 depots weekly for 3 mos. then 90cc a day 20% Glucosamine per oral | Improved stool consistency and lower frequency shrinkage of pseudo polyps |
| 7. RG Female Age 50 | Ulcerative Colitis Biopsy proven - total colonic involvement - oral corticosteroids and azulfidine ineffective | 30cc 20% Glucosamine HCL three times a day for 3 days per oral then two times a day for two weeks per oral | Complete Remission in ten days |
| 8. EP Female Age 76 | Ulcerative Colitis Prednisone & Azulfidine Ineffective | 90 cc 20% Glucosamine HCL each day for four days then 60 cc per day for 3 weeks (all per oral) | Marked improvement Sigmoidoscopically non-friable & decreased frequency |
| 9. SF Male Age 30 | Ulcerative Colitis | 40cc Glucosamine HCL (10%) in each of two depots once every two weeks for 6 weeks, then once every three weeks for 4 months | 24 lb weight gain Complete remission |

In none of the preceding cases was any evidence of toxicity (as determined clinically or by conventional laboratory tests) found. In several of the above cases complete freedom from disease was obtained for extended intervals up to several months or longer following termination of D-glucosamine therapy after long term treatment with corticosteroids had failed to provide relief. It will be appreciated that the present invention is not limited to use of D-glucosamine salts of pharmaceutically acceptable acids alone and other adjuvants such as vitamins, therapeutically effective medications, and the like may be administered together or in sequence with the active ingredients.

What is claimed is:

1. A method of treating ulcerative colitis in a mammal afflicted with said condition which comprises administering to said mammal an effective amount for treating ulcerative colitis of a composition containing d-glucosamine.

2. A method according to claim 1 which comprises orally administering said composition to said mammal.

3. A method according to claim 1 which comprises parenterally administering said composition to said mammal.

4. A method according to claim 2 which comprises administering D-glucosamine as the salt of a pharmaceutically acceptable acid.

5. A method according to claim 4 wherein said pharmaceutically acceptable acid salt of D-glucosamine comprises D-glucosamine hydrochloride.

6. A method according to claim 4 wherein said effective amount comprises from about 20 milligrams to about 300 milligrams of D-glucosamine hydrochloride per kilogram of body weight per day.

7. A method as recited in claim 6 wherein said effective amount comprises from about 50 milligrams to about 150 milligrams per kilogram of body weight per day of D-glucosamine hydrochloride.

8. A method of treating regional enteritis in a mammal afflicted with said condition which comprises administering to said mammal an effective amount for treating regional enteritis of a composition containing d-glucosamine.

9. A method according to claim 8 which comprises parenterally administering said composition to said mammal.

10. A method according to claim 8 which comprises orally administering said composition to said mammal.

11. A method according to claim 10 which comprises administering d-glucosamine as the salt of a pharmaceutically acceptable acid.

12. A method according to claim 11 wherein said pharmaceuticaly acceptable acid salt of d-glucosamine comprises d-glucosamine hydrochloride.

13. A method according to claim 12 wherein said effective amount comprises about 20 milligrams to about 300 milligrams of d-glucosamine hydrochloride per kilogram of body weight per day.

14. A method as recited in claim 13 wherein said effective amount comprises from about 50 milligrams to about 150 milligrams of d-glucosamine hydrochloride per kilogram of body weight per day.

15. A method according to claim 12 wherein said effective amount is administered in a solid form selected from the group consisting of a tablet and a capsule.

16. A method as recited in claim 12 wherein said effective amount is administered in a liquid dosage form.

17. A method as recited in claim 6 wherein said effective amount is administered in solid form selected from a tablet and a capsule.

18. A method as recited in claim 6 wherein said effective amount is administered in a liquid dosage form.

* * * * *